United States Patent
Leuwer et al.

(10) Patent No.: US 10,449,198 B2
(45) Date of Patent: *Oct. 22, 2019

(54) METHOD FOR TREATING PAIN

(71) Applicant: The University of Liverpool, Liverpool (GB)

(72) Inventors: Martin Leuwer, Liverpool (GB); Paul O'Neill, Liverpool (GB); Neil Berry, Liverpool (GB); Chandrakala Pidathala, Liverpool (GB)

(73) Assignee: The University of Liverpool, Liverpool (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/641,751

(22) Filed: Jul. 5, 2017

(65) Prior Publication Data

US 2018/0140608 A1    May 24, 2018

Related U.S. Application Data

(60) Provisional application No. 62/357,840, filed on Jul. 1, 2016.

(51) Int. Cl.
| | |
|---|---|
| *A61K 31/5375* | (2006.01) |
| *A61K 31/397* | (2006.01) |
| *A61K 31/495* | (2006.01) |
| *A61K 31/4453* | (2006.01) |
| *A61K 31/40* | (2006.01) |

(52) U.S. Cl.
CPC ........ *A61K 31/5375* (2013.01); *A61K 31/397* (2013.01); *A61K 31/40* (2013.01); *A61K 31/4453* (2013.01); *A61K 31/495* (2013.01)

(58) Field of Classification Search
CPC .. A61K 31/397; A61K 31/40; A61K 31/4453; A61K 31/495; A61K 31/5375
See application file for complete search history.

(56) References Cited

U.S. PATENT DOCUMENTS

| | | |
|---|---|---|
| 4,128,664 A | 12/1978 | Moore |
| 4,829,061 A | 5/1989 | Wolf et al. |
| 5,281,623 A | 1/1994 | Clemens et al. |
| 5,552,439 A | 9/1996 | Panetta |
| 9,676,786 B2 | 6/2017 | Leuwer et al. |
| 2005/0182041 A1 | 8/2005 | Altisen et al. |
| 2007/0093469 A1 | 4/2007 | Altisen et al. |
| 2007/0142477 A1 | 6/2007 | Leuwer et al. |
| 2012/0029235 A1 | 2/2012 | Leuwer et al. |
| 2017/0298076 A1 | 10/2017 | Leuwer et al. |

FOREIGN PATENT DOCUMENTS

| | | |
|---|---|---|
| DE | 3702755 A1 | 8/1988 |
| WO | 2005063665 A1 | 7/2005 |
| WO | 2005077896 A1 | 8/2005 |
| WO | 2007071967 A2 | 6/2007 |
| WO | 2010067069 A1 | 6/2010 |
| WO | 2015097475 A1 | 7/2015 |

*Primary Examiner* — Umamaheswari Ramachandran
(74) *Attorney, Agent, or Firm* — Barnes & Thornburg LLP

(57) ABSTRACT

The present invention relates to a method of treating pain in a patient in need of such treatment, said method comprising administering to said patient a therapeutically effective amount of a compound of formula (I) or a pharmaceutically acceptable salt or solvate:

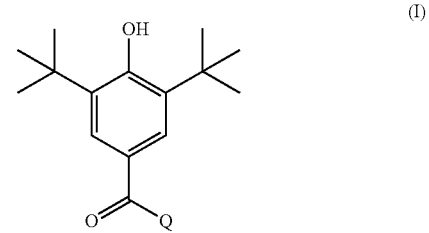

wherein Q is as defined herein.

22 Claims, 4 Drawing Sheets

METHOD FOR TREATING PAIN

CROSS-REFERENCE TO RELATED APPLICATIONS

This application claims the benefit to the U.S. Provisional Patent Application Ser. No. 62/357,840, filed Jul. 1, 2016, the entire disclosure of which is hereby expressly incorporated by reference in this Application

INTRODUCTION

The present invention relates to a method of treating pain (such as, for example, chronic pain or neuropathic pain) in a patient in need of such treatment, said method comprising administering to said patient a therapeutically effective amount of a compound as defined herein.

BACKGROUND OF THE INVENTION

In many clinical settings there is a need for safe and effective pain control strategies. However the majority of developments in the pain control field have failed to deliver high efficacy products free of undesirable side effects and safety issues. The opiates are generally regarded as the most effective treatment available for severe pain, but the ultimate goal is to deliver a pain control agent with the efficacy of the opiates but without the sedation, dependence, gastric damage and general tolerability problems that are associated with opiate use.

It has been postulated that phenol derivatives may have a number of neuromodulatory effects. However the only phenol derivative in widespread clinical use is the anaesthetic propofol (2,6-di-isopropylphenol).

Key features of anaesthesia are loss of consciousness, immobility in the presence of painful stimuli and absence of recall. Anaesthetics, such as propofol, are understood to mediate their anaesthetic effect by activating γ-aminobutyric acid (GABA$_A$) receptors in the Central Nervous System (CNS).

Analgesia is defined as the relief of pain. Among other peripheral and/or central nervous mechanisms, analgesia can arise as a result of enhanced inhibitory synaptic transmission within the dorsal horn of the spinal cord. It is understood that inhibitory postsynaptic transmission in the spinal cord involves mainly glycine receptors. Accordingly the glycine receptor family represents a target site for therapeutic agents aiming at inhibiting pain.

Both, GABA$_A$ and glycine receptors belong to the ligand-gated ion channel superfamily. They have a common structure in which five subunits form an ion channel. α and β subunits assemble into a pentameric receptor with a proposed in vivo stoichiometry of 3α: 2β. Glycine receptors, like GABA$_A$ receptors, inhibit neuronal firing by opening chloride channels following agonist binding. Glycine receptors are mainly found in lower areas of the central nervous system and are involved in the control of motor rhythm generation, the coordination of spinal nociceptive reflex responses and the processing of sensory signals.

Chronic pain is very different from acute pain. Acute pain can be considered as a useful early warning system informing us about noxious stimuli and thereby helping us to escape and prevent damage. Chronic pain, in contrast, is a disease in its own right. Experts regard it as a dys-equilibrium syndrome, where inhibitory neuronal activity which under normal circumstances suppresses the processing of pain is markedly reduced. Treatment of chronic inflammatory or neuropathic pain is still difficult, and there is currently no single treatment that works for all conditions.

Increased neuronal excitability seen in chronic pain involves a loss of inhibition mediated by GABA- and/or glycinergic neurons in the superficial dorsal horn of the spinal cord that control the relay of nociceptive signals from the periphery to higher areas of the central nervous system. In the adult dorsal horn, the contribution of glycine to fast inhibitory postsynaptic transmission dominates. Glycine receptors are mainly found in lower areas of the central nervous system and are involved in the control of motor rhythm generation, the coordination of spinal nociceptive reflex responses and the processing of sensory signals. Their role in modulating ascending nociceptive pathways and pain makes them a potentially interesting target site for analgesic and spasmolytic agents. Microinjection of the glycine receptor agonist taurine into the anterior cingulate cortex—associated with the affective component of pain—relieves neuropathic pain, an effect that could be antagonized by the selective glycine receptor antagonist strychnine. There are four α-subunits and one β-subunit for the strychnine-sensitive glycine receptor, the α1-subunit is widely expressed in the adult spinal cord and brain stem, but also in higher centres of the brain involved in sensory processing. The glycine receptor α3-subunit has been identified as a target site underlying central inflammatory pain sensitization due to PGE$_2$-induced receptor phosphorylation. α3-subunit knock-out mice do not develop inflammatory pain with otherwise normal response to acute pain. This phenomenon may be explained by the fact that α1 containing glycine receptor subunits which probably compensate for the lack in α3 do not possess the protein kinase A (PKA) phosphorylation site involved in the PGE$_2$ signal transduction. Furthermore, phosphorylation of the α3 subunit is not necessarily involved in neuropathic pain. Based on this understanding, a need has been identified by the inventors for the development of drugs that target the predominant adult glycine receptor isoform containing the α1 subunit. Given the physiological role of glycine receptors and their relatively restricted expression (mainly in the spinal cord and lower brain areas), a selective glycine modulator should be of great interest therapeutically to increase inhibition at the level of the spinal cord dorsal horn.

There exists a need to develop new and improved analgesic therapies. Despite the fact that glycine receptors represent a good target for identifying such analgesics, there are no existing analgesics that effectively target these receptors. The inventors therefore decided to address this issue and exploited their knowledge of the pathophysiological mechanisms underlying anaesthesia and analgesia with a view to identifying new and improved methods of treatment for controlling pain.

Aspects of the invention were devised with the foregoing in mind.

SUMMARY OF THE INVENTION

In one aspect, the present invention provides a method of treating a disease or condition in which the selective, positive allosteric modulation of strychnine-sensitive alpha 1-glycine receptors is beneficial in a patient in need of such treatment, said method comprising administering to said patient a therapeutically effective amount of a compound of formula (I) as defined herein, or a pharmaceutically acceptable salt or solvate thereof, or a pharmaceutical composition as defined herein.

In another aspect, the present invention provides a method of treating pain in a patient in need of such treatment, said method comprising administering to said patient a therapeutically effective amount of a compound of formula (I) as defined herein, or a pharmaceutically acceptable salt or solvate thereof, or a pharmaceutical composition as defined herein.

In another aspect, the present invention provides a method of treating chronic pain in a patient in need of such treatment, said method comprising administering to said patient a therapeutically effective amount of a compound of formula (I) as defined herein, or a pharmaceutically acceptable salt or solvate thereof, or a pharmaceutical composition as defined herein.

In another aspect, the present invention provides a method of treating neuropathic pain in a patient in need of such treatment, said method comprising administering to said patient a therapeutically effective amount of a compound of formula (I) as defined herein, or a pharmaceutically acceptable salt or solvate thereof, or a pharmaceutical composition as defined herein.

In another aspect, the present invention provides a method of treating chronic neuropathic pain in a patient in need of such treatment, said method comprising administering to said patient a therapeutically effective amount of a compound of formula (I) as defined herein, or a pharmaceutically acceptable salt or solvate thereof, or a pharmaceutical composition as defined herein.

In another aspect, the present invention provides a compound of formula (I) as defined herein, or a pharmaceutically acceptable salt or solvate thereof, or a pharmaceutical composition as defined herein for use in the treatment of a disease or condition in which the selective, positive allosteric modulation of strychnine-sensitive alpha 1-glycine receptors is beneficial.

In another aspect, the present invention provides a compound of formula (I) as defined herein, or a pharmaceutically acceptable salt or solvate thereof, or a pharmaceutical composition as defined herein for use in the treatment of pain.

In another aspect, the present invention provides a compound of formula (I) as defined herein, or a pharmaceutically acceptable salt or solvate thereof, or a pharmaceutical composition as defined herein for use in the treatment of chronic pain.

In another aspect, the present invention provides a compound of formula (I) as defined herein, or a pharmaceutically acceptable salt or solvate thereof, or a pharmaceutical composition as defined herein for use in the treatment of neuropathic pain.

In another aspect, the present invention provides a compound of formula (I) as defined herein, or a pharmaceutically acceptable salt or solvate thereof, or a pharmaceutical composition as defined herein for use in the treatment of chronic neuropathic pain.

In another aspect, the present invention provides the use of a compound of formula (I) as defined herein, or a pharmaceutically acceptable salt or solvate thereof, or a pharmaceutical composition as defined herein, in the manufacture of a medicament for use in the treatment of a disease or condition in which the selective, positive allosteric modulation of strychnine-sensitive alpha 1-glycine receptors is beneficial.

In another aspect, the present invention provides the use of a compound of formula (I) as defined herein, or a pharmaceutically acceptable salt or solvate thereof, or a pharmaceutical composition as defined herein, in the manufacture of a medicament for use in the treatment of pain.

In another aspect, the present invention provides the use of a compound of formula (I) as defined herein, or a pharmaceutically acceptable salt or solvate thereof, or a pharmaceutical composition as defined herein, in the manufacture of a medicament for use in the treatment of chronic pain.

In another aspect, the present invention provides the use of a compound of formula (I) as defined herein, or a pharmaceutically acceptable salt or solvate thereof, or a pharmaceutical composition as defined herein, in the manufacture of a medicament for use in the treatment of neuropathic pain.

In another aspect, the present invention provides the use of a compound of formula (I) as defined herein, or a pharmaceutically acceptable salt or solvate thereof, or a pharmaceutical composition as defined herein, in the manufacture of a medicament for use in the treatment of chronic neuropathic pain.

DETAILED DESCRIPTION OF THE INVENTION

Definitions

Figure 1:
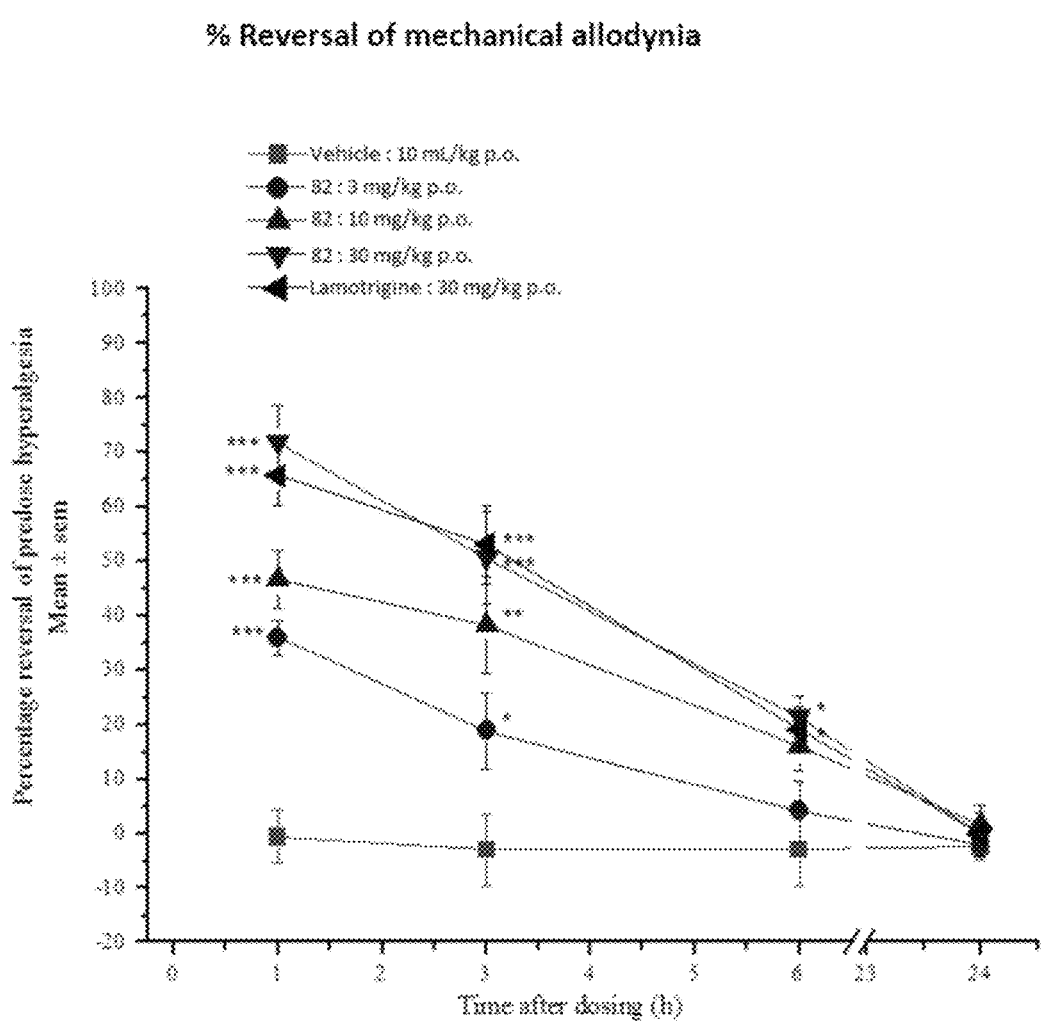
FIG. 1 shows the effect of compound 82 on ipsilateral paw withdrawal thresholds to mechanical pressure in neuropathic rats in comparison with lamotrigine. Fasted, male, Wistar rats. n=6/group. Vehicle: 10% DMSO/10% Solutol HS15/80% saline. 10 ml/kg p.o. One-way ANOVA, comparison with time-matched vehicle group using Tukey's HSD test, *$p<0.05$, $p<0.01$, *$p<0.001$

Unless otherwise stated, the following terms used in the specification and claims have the following meanings set out below.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

The term "halo" refers to fluoro, chloro, bromo and iodo.

The phrase "method of the invention" means those methods which are disclosed herein, both generically and specifically.

Compounds of Formula (I)

In each aspect of the invention, said methods/uses comprise administering to said patient a therapeutically effective amount of a compound of formula (I) or a pharmaceutically acceptable salt thereof:

(I)

wherein:
Q is selected from:

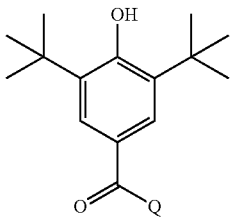
(i)

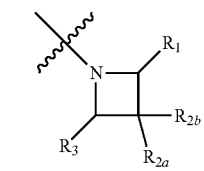
(iia)

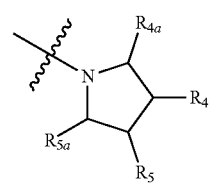
(iiia)

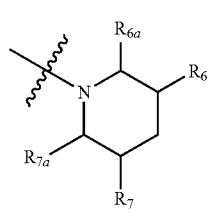
(iva)

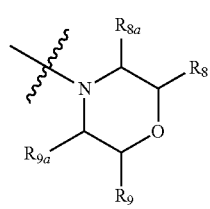

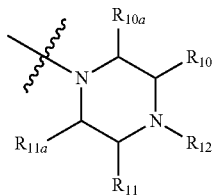
(va)

wherein:
$R_1$, $R_{2a}$, $R_{2b}$ and $R_3$ are each independently selected from hydrogen, halo, hydroxy, a linear or branched, saturated or unsaturated (1-8C) aliphatic group, an —O(1-8C) alkyl group, an amino group, a —CO—NH$_2$ group, a —CO—NH-(1-8C alkyl) group, a —CO—N-(1-80 alkyl)$_2$ group an —NH—CO-(1-8C alkyl) group, a carboxy group, and an aryl group, wherein said aliphatic group, —O(1-8C) alkyl group, —CO—NH-(1-8C alkyl) group, —CO—N-(1-8C alkyl)$_2$ group, —NH—CO-(1-8C alkyl) group and aryl group may be optionally substituted with one or more groups selected from halo, (1-4C) alkyl, and hydroxy; or $R_{2a}$ and $R_{2b}$ are linked such that together they form a 4, 5 or 6-membered carbocyclic or heterocyclic ring;

$R_4$, $R_{4a}$, $R_5$ and $R_{5a}$ are each independently selected from hydrogen, halo, hydroxy, a linear or branched, saturated or unsaturated (1-8C) aliphatic group, an —O(1-8C) alkyl group, an amino group, a —CO—NH$_2$ group, a —CO—NH-(1-8C alkyl) group, a —CO—N-(1-8C alkyl)$_2$ group an —NH—CO-(1-8C alkyl) group, a carboxy group, and an aryl group, wherein said aliphatic group, —O(1-8C) alkyl group, —CO—NH-(1-8C alkyl) group, —CO—N-(1-8C alkyl)$_2$ group, —NH—CO-(1-8C alkyl) group and aryl group may be optionally substituted with one or more groups selected from halo, (1-4C) alkyl, and hydroxy;

$R_6$, $R_{6a}$, $R_7$ and $R_{7a}$ are each independently selected from hydrogen, halo, hydroxy, a linear or branched, saturated or unsaturated (1-8C) aliphatic group, an —O(1-8C) alkyl group, an amino group, a —CO—NH$_2$ group, a —CO—NH-(1-8C alkyl) group, a —CO—N-(1-8C alkyl)$_2$ group an —NH—CO-(1-8C alkyl) group, a carboxy group, and an aryl group, wherein said aliphatic group, —O(1-8C) alkyl group, —CO—NH-(1-8C alkyl) group, —CO—N-(1-8C alkyl)$_2$ group, —NH—CO-(1-8C alkyl) group and aryl group may be optionally substituted with one or more groups selected from halo, (1-4C) alkyl, and hydroxy;

$R_8$, $R_{8a}$, $R_9$ and $R_{9a}$ are each independently selected from hydrogen, halo, hydroxy, a linear or branched, saturated or unsaturated (1-8C) aliphatic group, an —O(1-8C) alkyl group, an amino group, a —CO—NH$_2$ group, a —CO—NH-(1-8C alkyl) group, a —CO—N-(1-8C alkyl)$_2$ group an —NH—CO-(1-8C alkyl) group, a carboxy group, and an aryl group, wherein said aliphatic group, —O(1-8C) alkyl group, —CO—NH-(1-8C alkyl) group, —CO—N-(1-8C alkyl)$_2$ group, —NH—CO-(1-8C alkyl) group and aryl group may be optionally substituted with one or more groups selected from halo, (1-4C) alkyl, and hydroxy;

$R_{10}$, $R_{10a}$, $R_{11}$ and $R_{11a}$ are each independently selected from hydrogen, halo, hydroxy, a linear or branched, saturated or unsaturated (1-8C) aliphatic group, an —O(1-8C) alkyl group, an amino group, a —CO—NH$_2$ group, a —CO—NH-(1-8C alkyl) group, a —CO—N-(1-8C alkyl)₂ group an —NH—CO-(1-8C alkyl) group, a carboxy group, and an aryl group, wherein said aliphatic group, —O(1-8C) alkyl group, —CO—NH-(1-8C alkyl) group, —CO—N-(1-8C alkyl)₂ group, —NH—CO-(1-8C alkyl) group and aryl group may be optionally substituted with one or more groups selected from halo, (1-4C) alkyl, and hydroxy; and R₁₂ is selected from hydrogen, (1-6C)alkyl and (1-6C) haloalkyl.

In the compounds of formula I above, ∿∿∿ indicates the bond that attaches Q to the C(=O) moiety of the compound of formula I. In all cases, Q is a nitrogen linked heterocyclic ring of the formula (i), (iia), (iiia), (iva) or (va) shown above.

Each of the embodiments below are applicable to each aspect of the invention.

In one embodiment, the compound of formula (I) comprises a Q group selected from (iia), (iiia), (iva) and (va).

In another embodiment, the compound of formula (I) comprises a Q group selected from (iia), (iiia), and (iva).

In another embodiment, the compound of formula (I) comprises a Q group selected from (iiia), (iva), and (va).

In another embodiment, the compound of formula (I) comprises a Q group selected from (iiia) and (iva).

In another embodiment, the compound of formula (I) comprises a Q group selected from (iva) and (va).

In another embodiment, the compound of formula (I) comprises a Q group (iva).

In another embodiment, the compound of formula (I) comprises R₁, R₂ₐ, R₂ᵦ, R₂, R₃, R₄, R₅, R₆, R₇, R₈, R₉, R₁₀, R₁₁ and R₁₂ groups wherein:

R₁, R₂ₐ, R₂ᵦ and R₃ are each independently selected from hydrogen, halo, hydroxy, a linear or branched, saturated or unsaturated (1-6C) aliphatic group, an —O(1-6C) alkyl group, and an amino group, wherein said aliphatic group, —O(1-6C) alkyl group, may be optionally substituted with one or more groups selected from halo, (1-4C) alkyl, and hydroxy; or R₂ₐ and R₂ᵦ are linked such that together they form a 4, 5 or 6-membered carbocyclic or heterocyclic ring;

R₄, R₄ₐ, R₅ and R₅ᵦ are each independently selected from hydrogen, halo, hydroxy, a linear or branched, saturated or unsaturated (1-6C) aliphatic group, an —O(1-6C) alkyl group, and an amino group, wherein said aliphatic group, —O(1-6C) alkyl group, may be optionally substituted with one or more groups selected from halo, (1-4C) alkyl, and hydroxy;

R₆, R₆ₐ, R₇ and R₇ₐ are each independently selected from hydrogen, halo, hydroxy, a linear or branched, saturated or unsaturated (1-6C) aliphatic group, an —O(1-6C) alkyl group, and an amino group, wherein said aliphatic group, —O(1-6C) alkyl group, may be optionally substituted with one or more groups selected from halo, (1-4C) alkyl, and hydroxy;

R₈, R₈ₐ, R₉ and R₉ₐ are each independently selected from hydrogen, halo, hydroxy, a linear or branched, saturated or unsaturated (1-6C) aliphatic group, an —O(1-6C) alkyl group, and an amino group, wherein said aliphatic group, —O(1-6C) alkyl group, may be optionally substituted with one or more groups selected from halo, (1-4C) alkyl, and hydroxy;

R₁₀, R₁₀ₐ, R₁₁ and R₁₁ₐ are each independently selected from hydrogen, halo, hydroxy, a linear or branched, saturated or unsaturated (1-6C) aliphatic group, an —O(1-6C) alkyl group, and an amino group, wherein said aliphatic group, —O(1-6C) alkyl group, may be optionally substituted with one or more groups selected from halo, (1-4C) alkyl, and hydroxy; and R₁₂ is selected from hydrogen, (1-4C)alkyl and (1-4C) haloalkyl.

In another embodiment of each method, the compound of formula (I) comprises R₁, R₂ₐ, R₂ᵦ, R₂, R₃, R₄, R₅, R₆, R₇, R₈, R₉, R₁₀, R₁₁ and R₁₂ groups wherein:

R₁, R₂ₐ, R₂ᵦ and R₃ are each independently selected from hydrogen, halo, methyl, hydroxymethyl, CF₃ and OCF₃; or R₂ₐ and R₂ᵦ are linked such that together they form a 4,5 or 6-membered carbocyclic or heterocyclic ring;

R₄, R₄ₐ, R₅ and R₅ᵦ are each independently selected from hydrogen, halo, methyl, hydroxymethyl, CF₃ and OCF₃;

R₆, R₆ₐ, R₇ and R₇ₐ are each independently selected from hydrogen, halo, methyl, hydroxymethyl, CF₃ and OCF₃;

R₈, R₈ₐ, R₉ and R₉ₐ are each independently selected from hydrogen, methyl, CF₃ halo, hydroxymethyl and OCF₃;

R₁₀, R₁₀ₐ, R₁₁ and R₁₁ₐ are each independently selected from hydrogen, methyl, CF₃ halo, hydroxymethyl and OCF₃; and R₁₂ is selected from hydrogen, (1-4C)alkyl or (1-4C) haloalkyl.

In another embodiment, the compound of formula (I) comprises a Q group selected from

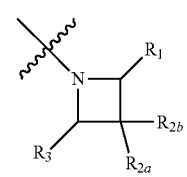

(i)

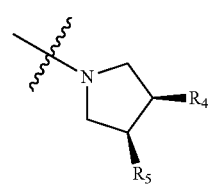

(ii)

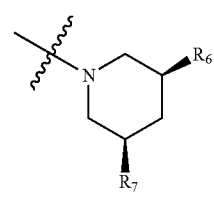

(iii)

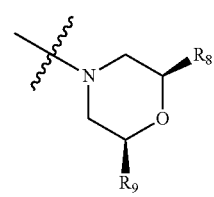

(iv)

-continued

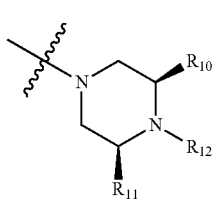
(v)

In one embodiment, the compound of formula (I) comprises a Q group selected from (ii), (iii), (iv) and (v).

In another embodiment, the compound of formula (I) comprises a Q group selected from (ii), (iii), and (iv).

In another embodiment, the compound of formula (I) comprises a Q group selected from (iii), (iv), and (v).

In another embodiment, the compound of formula (I) comprises a Q group selected from (iii) and (iv).

In another embodiment, the compound of formula (I) comprises a Q group selected from (iv) and (v).

In another embodiment, the compound of formula (I) comprises a Q group (iv).

In another embodiment, the compound of formula (I) comprises $R_1$, $R_{2a}$, $R_{2b}$, $R_2$, $R_3$, $R_4$, $R_5$, $R_6$, $R_7$, $R_8$, $R_9$, $R_{10}$, $R_{11}$ and $R_{12}$ groups wherein:

$R_1$, $R_{2a}$, $R_{2b}$ and $R_3$ are each independently selected from hydrogen, halo, hydroxy, a linear or branched, saturated or unsaturated (1-6C) aliphatic group, an —O(1-6C) alkyl group, and an amino group, wherein said aliphatic group, —O(1-6C) alkyl group, may be optionally substituted with one or more groups selected from halo, (1-4C) alkyl, and hydroxy; or $R_{2a}$ and $R_{2b}$ are linked such that together they form a 4, 5 or 6-membered carbocyclic or heterocyclic ring;

$R_4$ and $R_5$ are each independently selected from hydrogen, halo, hydroxy, a linear or branched, saturated or unsaturated (1-6C) aliphatic group, an —O(1-6C) alkyl group, and an amino group, wherein said aliphatic group, —O(1-6C) alkyl group, may be optionally substituted with one or more groups selected from halo, (1-4C) alkyl, and hydroxy;

$R_6$ and $R_7$ are each independently selected from hydrogen, halo, hydroxy, a linear or branched, saturated or unsaturated (1-6C) aliphatic group, an —O(1-6C) alkyl group, and an amino group, wherein said aliphatic group, —O(1-6C) alkyl group, may be optionally substituted with one or more groups selected from halo, (1-4C) alkyl, and hydroxy;

$R_8$ and $R_9$ are each independently selected from hydrogen, halo, hydroxy, a linear or branched, saturated or unsaturated (1-6C) aliphatic group, an —O(1-6C) alkyl group, and an amino group, wherein said aliphatic group, —O(1-6C) alkyl group, may be optionally substituted with one or more groups selected from halo, (1-4C) alkyl, and hydroxy;

$R_{10}$ and $R_{11}$ are each independently selected from hydrogen, halo, hydroxy, a linear or branched, saturated or unsaturated (1-6C) aliphatic group, an —O(1-6C) alkyl group, and an amino group, wherein said aliphatic group, —O(1-6C) alkyl group, may be optionally substituted with one or more groups selected from halo, (1-4C) alkyl, and hydroxy; and $R_{12}$ is selected from hydrogen, (1-4C)alkyl and (1-4C) haloalkyl.

In another embodiment of each method, the compound of formula (I) comprises $R_1$, $R_{2a}$, $R_{2b}$, $R_2$, $R_3$, $R_4$, $R_5$, $R_6$, $R_7$, $R_8$, $R_9$, $R_{10}$, $R_{11}$ and $R_{12}$ groups wherein:

$R_1$, $R_{2a}$, $R_{2b}$ and $R_3$ are each independently selected from hydrogen, halo, methyl, hydroxymethyl, $CF_3$ and $OCF_3$; or $R_{2a}$ and $R_{2b}$ are linked such that together they form a 4, 5 or 6-membered carbocyclic or heterocyclic ring;

$R_4$ and $R_5$ are each independently selected from hydrogen, halo, methyl, hydroxymethyl, $CF_3$ and $OCF_3$;

$R_6$ and $R_7$ are each independently selected from hydrogen, halo, methyl, hydroxymethyl, $CF_3$ and $OCF_3$;

$R_8$ and $R_9$ are each independently selected from hydrogen, methyl, $CF_3$ halo, hydroxymethyl and $OCF_3$;

$R_{10}$ and $R_{11}$ are each independently selected from hydrogen, methyl, $CF_3$ halo, hydroxymethyl and $OCF_3$; and $R_{12}$ is selected from hydrogen, (1-4C)alkyl or (1-4C) haloalkyl.

In further embodiments, compounds of formula (I) are further defined based on any of the following numbered paragraphs:

1. Q is selected from:

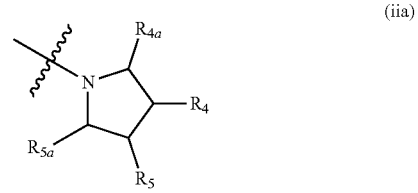
(iia)

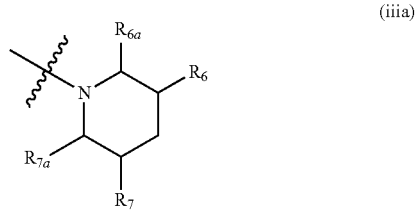
(iiia)

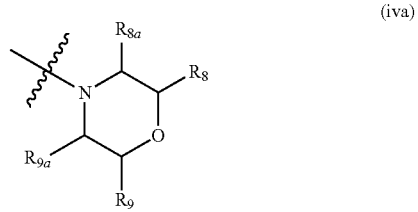
(iva)

2. Q is selected from:

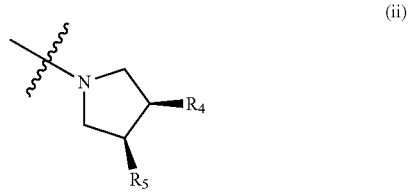
(ii)

-continued

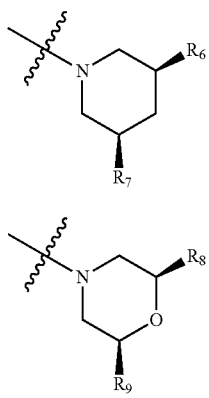

3. Q is selected from:

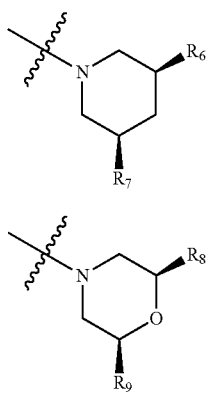

4. Q is:

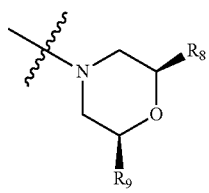

5. Q is of formula (i) and $R_1$, $R_2$, $R_{2a}$, $R_{2b}$ and $R_3$ are each independently selected from hydrogen, halo, methyl, hydroxymethyl, $CF_3$ and $OCF_3$; or $R_{2a}$ and $R_{2b}$ are linked such that together they form a 4 or 5 membered carbocyclic or heterocyclic ring;
6. Q is of formula (i) and one of $R_{2a}$ or $R_{2b}$ is hydrogen and the other is selected from hydrogen, fluoro, methyl, hydroxymethyl, $CF_3$ and $OCF_3$; or $R_{2a}$ and $R_{2b}$ are linked such that together they form a 4 membered heterocyclic ring comprising one N or O atom;
7. $R_1$, $R_{2a}$, $R_{2b}$ $R_2$ and $R_3$ are each independently selected from hydrogen, fluoro, methyl, hydroxymethyl, $CF_3$ and $OCF_3$;
8. $R_1$, $R_{2a}$, $R_{2b}$ $R_2$ and $R_3$ are each independently selected from hydrogen, fluoro, methyl, hydroxymethyl, $CF_3$ and $OCF_3$;
9. $R_1$, $R_{2a}$, $R_{2b}$, $R_2$ and $R_3$ are each independently selected from hydrogen, fluoro or methyl;
10. $R_1$, $R_{2a}$, $R_{2b}$ $R_2$ and $R_3$ are all hydrogen;
11. one or two of $R_1$, $R_{2a}$, $R_{2b}$, $R_2$ and $R_3$ is a substituent other than hydrogen;
12. one of $R_1$, $R_{2a}$, $R_{2b}$, $R_2$ and $R_3$ is a substituent other than hydrogen.
13. $R_1$ and $R_3$ are each independently selected from hydrogen, fluoro or methyl and $R_{2a}$ and $R_{2b}$ are hydrogen;
14. $R_{2a}$ and $R_{2b}$ are hydrogen and one of $R_1$ and $R_3$ is selected from hydrogen, fluoro or methyl and the other is hydrogen;
15. $R_1$, $R_{2a}$ and $R_3$ are hydrogen and $R_{2b}$ is selected from hydrogen, fluoro, methyl, hydroxymethyl, $CF_3$ and $OCF_3$;
16. $R_1$, $R_{2a}$ and $R_3$ are hydrogen and $R_{2b}$ is fluoro;
17. $R_1$ and $R_3$ are hydrogen and $R_{2a}$ and $R_{2b}$ are linked such that together they form a 4 membered carbocyclic or heterocyclic ring;
18. $R_4$, $R_{4a}$, $R_5$ and $R_{5a}$ are each independently selected from hydrogen, fluoro, methyl, hydroxymethyl, $CF_3$ and $OCF_3$;
19. $R_4$, $R_{4a}$, $R_5$ and $R_{5a}$ are each independently selected from hydrogen, fluoro or methyl;
20. $R_4$, $R_{4a}$, $R_5$ and $R_{5a}$ are all hydrogen;
21. $R_4$ and $R_5$ are each independently selected from hydrogen, fluoro, methyl, hydroxymethyl, $CF_3$ and $OCF_3$;
22. $R_4$ and $R_5$ are each independently selected from hydrogen, fluoro or methyl;
23. $R_4$ and $R_5$ are both hydrogen;
24. one of $R_4$ and $R_5$ is fluoro or methyl and the other is hydrogen;
25. $R_6$, $R_{6a}$, $R_7$ and $R_{7a}$ are each independently selected from hydrogen, fluoro, methyl, hydroxymethyl, $CF_3$ and $OCF_3$;
26. $R_6$, $R_{6a}$, $R_7$ and $R_{7a}$ are each independently selected from hydrogen, fluoro or methyl;
27. $R_6$, $R_{6a}$, $R_7$ and $R_{7a}$ are all hydrogen;
28. $R_6$ and $R_7$ are each independently selected from hydrogen, fluoro, methyl, hydroxymethyl, $CF_3$ and $OCF_3$;
29. $R_6$ and $R_7$ are each independently selected from hydrogen, fluoro or methyl;
30. $R_6$ and $R_7$ are both hydrogen;
31. one of $R_6$ and $R_7$ is fluoro or methyl and the other is hydrogen.
32. $R_8$, $R_{8a}$, $R_9$ and $R_{9a}$ are each independently selected from hydrogen or methyl;
33. $R_8$, $R_{8a}$, $R_9$ and $R_{9a}$ are all hydrogen;
34. $R_8$ and $R_9$ are each independently selected from hydrogen or methyl;
35. $R_8$ and $R_9$ are both hydrogen;
36. one of $R_8$ and $R_9$ is methyl and the other is hydrogen;
37. $R_{10}$ and $R_{11}$ are each independently selected from hydrogen, fluoro or methyl;
38. $R_{10}$ and $R_{11}$ are both hydrogen;
39. one of $R_{10}$ and $R_{11}$ is methyl and the other is hydrogen;
40. $R_{10}$ and $R_{11}$ are both hydrogen and $R_{12}$ is methyl;
41. $R_{12}$ is selected from hydrogen or (1-4C)alkyl;
42. $R_{12}$ is methyl.

Suitably, Q is as defined in paragraphs (1), (2), (3) or (4) above. In an embodiment, Q has the structural formula (i). In another embodiment, Q has the structural formula (ii). In an embodiment, Q has the structural formula (iii). In a particular embodiment, Q has the structural formula (iv).

In a particular embodiment, Q is as defined in paragraph (4) above.

Suitably when Q is of formula (i), it has the formula shown below:

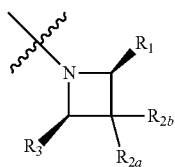
(i)

In a particular group of compounds of formula (I), Q is of the structural formula (iv) shown above. Such compounds have the structural formula IA below:

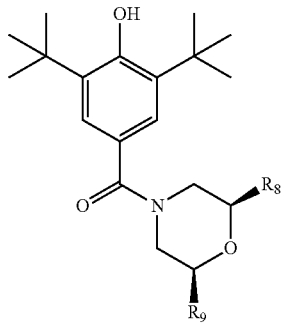
IA wherein $R_8$ and $R_9$ each have any one of the definitions set out herein.

In an embodiment of the compounds of formula IA, $R_8$ and $R_9$ are each independently selected from hydrogen or methyl.

In a further embodiment of the compounds of formula IA, $R_8$ and $R_9$ are both hydrogen.

In a further embodiment of the compounds of formula IA, one of $R_8$ and $R_9$ is methyl and the other is hydrogen.

In a particular group of compounds of formula (I), Q is of the structural formula (iva) shown above. Such compounds have the structural formula IB below:

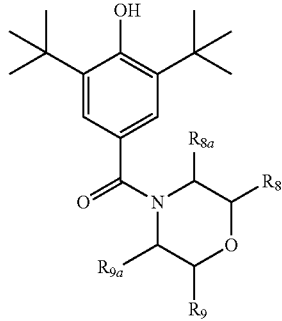
IB wherein $R_8$, $R_{8a}$, $R_9$ and $R_{9a}$ each have any one of the definitions set out herein.

In an embodiment of the compounds of formula IB, $R_8$, $R_{8a}$, $R_9$ and $R_{9a}$ are each independently selected from hydrogen or methyl.

In another embodiment of the compounds of formula IB, $R_{8a}$, $R_{9a}$ are each independently selected from hydrogen or methyl and $R_8$ and $R_9$ are both hydrogen.

Particular compounds of formula (I) include any one of the following:
(4-(hydroxy)-3,5-di-tert-butylphenyl)(morpholino)methanone;
(R)-(4-(hydroxy)-3,5-di-tert-butylphenyl)(2-methylmorpholino)methanone;
(3-fluoroazetidin-1-yl)(4-hydroxy-3,5-di-tert-butylphenyl)methanone;
(4-(benzyloxy)-3,5-di-tert-butylphenyl)(piperidin-1-yl)methanone;
(4-Hydroxy-3,5-di-tert-butylphenyl)(2-oxa-6-azaspiro[3.3]heptan-6-yl)methanone;
(4-Hydroxy-3,5-di-tert-butylphenyl)(4-methylpiperazin-1-yl)methanone;
or a pharmaceutically acceptable salt or solvate thereof.

In a particular embodiment, the compound of formula (I) is:
(4-(hydroxy)-3,5-di-tert-butylphenyl)(morpholino)methanone

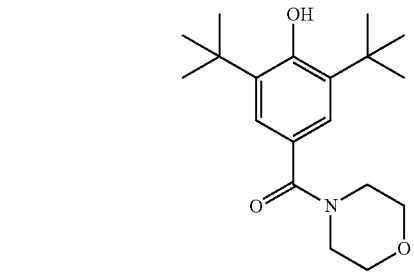 [SMILES: CC(C)(C)c1cc(C(=O)N2CCOCC2)cc(C(C)(C)C)c1O]

or a pharmaceutically acceptable salt or solvate thereof.

The various functional groups and substituents making up the compounds of the present invention are typically chosen such that the molecular weight of the compound does not exceed 1000. More usually, the molecular weight of the compound will be less than 750, for example less than 700, or less than 650, or less than 600, or less than 550. More preferably, the molecular weight is less than 525 and, for example, is 500 or less.

Suitable or preferred features of any compounds of formula (I) may also be suitable features of any other aspects of the invention.

A suitable pharmaceutically acceptable salt of a compound of formula (I) is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of formula (I) may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of formula (I) may have geometric isomeric centres (E- and Z-isomers). It is to be understood that the present invention encompasses all optical, diastereoisomers and geometric isomers and mixtures thereof that possess activity.

The methods of the present invention also encompasses administering compounds of formula (I) as defined herein which comprise one or more isotopic substitutions. For example, H may be in any isotopic form, including $^1H$, $^2H(D)$, and $^3H$ (T); C may be in any isotopic form, including $^{12}C$, $^{13}C$, and $^{14}C$; and O may be in any isotopic form, including $^{16}O$ and $^{18}O$; and the like.

It is also to be understood that certain compounds of formula (I) may exist in solvated as well as unsolvated forms such as, for example, hydrated forms. It is to be understood that the methods of the invention encompasses administering all such solvated forms that possess activity.

It is also to be understood that certain compounds of formula (I) may exhibit polymorphism, and that the methods of invention encompass administering all such forms that possess activity.

Compounds of formula (I) may exist in a number of different tautomeric forms and references to compounds of formula (I) include all such forms. For the avoidance of doubt, where a compound can exist in one of several tautomeric forms, and only one is specifically described or shown, all others are nevertheless embraced by compounds of formula (I). Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

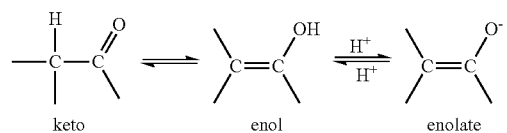

keto ⇌ enol ⇌ enolate

Compounds of formula (I) containing an amine function may also form N-oxides. A reference herein to a compound of the formula I that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example *Advanced Organic Chemistry, by Jerry March*, 4$^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

The compounds of formula (I) may be administered in the form of a pro-drug which is broken down in the human or animal body to release a compound of formula (I). A pro-drug may be used to alter the physical properties and/or the pharmacokinetic properties of a compound of the invention. A pro-drug can be formed when the compound of formula (I) contains a suitable group or substituent to which a property-modifying group can be attached. Examples of pro-drugs include in vivo cleavable ester derivatives that may be formed at a carboxy group or a hydroxy group in a compound of formula (I) and in-vivo cleavable amide derivatives that may be formed at a carboxy group or an amino group in a compound of formula (I).

Accordingly, the methods of the present invention include administering those compounds of the formula I as defined hereinbefore when made available by organic synthesis and when made available within the human or animal body by way of cleavage of a pro-drug thereof. Accordingly, the methods of the present invention include administering those compounds of the formula I that are produced by organic synthetic means and also such compounds that are produced in the human or animal body by way of metabolism of a precursor compound, that is a compound of the formula I may be a synthetically-produced compound or a metabolically-produced compound.

A suitable pharmaceutically acceptable pro-drug of a compound of the formula I is one that is based on reasonable medical judgement as being suitable for administration to the human or animal body without undesirable pharmacological activities and without undue toxicity.

Various forms of pro-drug have been described, for example in the following documents:—
a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);

e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

The in vivo effects of a compound of the formula I may be exerted in part by one or more metabolites that are formed within the human or animal body after administration of a compound of the formula I. As stated hereinbefore, the in vivo effects of a compound of the formula I may also be exerted by way of metabolism of a precursor compound (a pro-drug).

It shall also be appreciated that compounds of formula I may also be covalently linked (at any suitable position) to other groups such as, for example, solubilising moieties (for example, PEG polymers), moieties that enable them to be bound to a solid support (such as, for example, biotin-containing moieties), and targeting ligands (such as antibodies or antibody fragments).

Synthesis of Compounds of Formula (I)

The compounds of formula (I) can be synthesised using chemistry techniques that are known in the art.

In the description of the synthetic methods described below and in the referenced synthetic methods that are used to prepare the staring materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

It will be appreciated that during the synthesis of the compounds of formula (I) in the processes defined below, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example $BF_3.OEt_2$. A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

Pharmaceutical Compositions

In one embodiment, each of the methods of the present invention comprise administering a pharmaceutical composition comprising a compound of formula (I) as defined hereinbefore.

In one embodiment, the pharmaceutical composition comprise a compound of formula (I) as defined hereinbefore, or a pharmaceutically acceptable salt or solvate thereof, in association with a pharmaceutically acceptable diluent or carrier.

The compositions may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions may be obtained by conventional procedures using conventional pharmaceutical excipients, well known in the art. Thus, compositions intended for oral use may contain, for example, one or more colouring, sweetening, flavouring and/or preservative agents.

An effective amount of a compound of formula (I) or a pharmaceutical composition thereof for administration in a method of the invention is an amount sufficient to reduce in a patient, particularly a warm-blooded animal, more particularly a human, the severity of the symptoms presented.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the formula I will naturally vary according to the nature and severity of the conditions, the age and sex of the animal or patient and the route of administration, according to well-known principles of medicine.

In using a compound of formula (I) or a pharmaceutical composition thereof in a method of the invention for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of formula (I).

Therapeutic Uses and Methods

In one aspect, the present invention provides a method of treating a disease or condition in which the selective, positive allosteric modulation of strychnine-sensitive alpha 1-glycine receptors is beneficial in a patient in need of such treatment, said method comprising administering to said patient a therapeutically effective amount of a compound of formula (I) as defined herein, or a pharmaceutically acceptable salt or solvate thereof, or a pharmaceutical composition as defined herein.

In another aspect, the present invention provides a method of treating pain in a patient in need of such treatment, said method comprising administering to said patient a therapeutically effective amount of a compound of formula (I) as defined herein, or a pharmaceutically acceptable salt or solvate thereof, or a pharmaceutical composition as defined herein.

In another aspect, the present invention provides a method of treating chronic pain in a patient in need of such treatment, said method comprising administering to said patient a therapeutically effective amount of a compound of formula (I) as defined herein, or a pharmaceutically acceptable salt or solvate thereof, or a pharmaceutical composition as defined herein.

In another aspect, the present invention provides a method of treating neuropathic pain in a patient in need of such treatment, said method comprising administering to said patient a therapeutically effective amount of a compound of formula (I) as defined herein, or a pharmaceutically acceptable salt or solvate thereof, or a pharmaceutical composition as defined herein.

In another aspect, the present invention provides a method of treating chronic neuropathic pain in a patient in need of such treatment, said method comprising administering to said patient a therapeutically effective amount of a compound of formula (I) as defined herein, or a pharmaceutically acceptable salt or solvate thereof, or a pharmaceutical composition as defined herein.

In another aspect, the present invention provides a compound of formula (I) as defined herein, or a pharmaceutically acceptable salt or solvate thereof, or a pharmaceutical composition as defined herein for use in the treatment of a disease or condition in which the selective, positive allosteric modulation of strychnine-sensitive alpha 1-glycine receptors is beneficial.

In another aspect, the present invention provides a compound of formula (I) as defined herein, or a pharmaceutically acceptable salt or solvate thereof, or a pharmaceutical composition as defined herein for use in the treatment of pain.

In another aspect, the present invention provides a compound of formula (I) as defined herein, or a pharmaceutically acceptable salt or solvate thereof, or a pharmaceutical composition as defined herein for use in the treatment of chronic pain.

In another aspect, the present invention provides a compound of formula (I) as defined herein, or a pharmaceutically acceptable salt or solvate thereof, or a pharmaceutical composition as defined herein for use in the treatment of neuropathic pain.

In another aspect, the present invention provides a compound of formula (I) as defined herein, or a pharmaceutically acceptable salt or solvate thereof, or a pharmaceutical composition as defined herein for use in the treatment of chronic neuropathic pain.

In another aspect, the present invention provides the use of a compound of formula (I) as defined herein, or a pharmaceutically acceptable salt or solvate thereof, or a pharmaceutical composition as defined herein, in the manufacture of a medicament for use in the treatment of a disease or condition in which the selective, positive allosteric modulation of strychnine-sensitive alpha 1-glycine receptors is beneficial.

In another aspect, the present invention provides the use of a compound of formula (I) as defined herein, or a pharmaceutically acceptable salt or solvate thereof, or a pharmaceutical composition as defined herein, in the manufacture of a medicament for use in the treatment of pain.

In another aspect, the present invention provides the use of a compound of formula (I) as defined herein, or a pharmaceutically acceptable salt or solvate thereof, or a pharmaceutical composition as defined herein, in the manufacture of a medicament for use in the treatment of chronic pain.

In another aspect, the present invention provides the use of a compound of formula (I) as defined herein, or a pharmaceutically acceptable salt or solvate thereof, or a pharmaceutical composition as defined herein, in the manufacture of a medicament for use in the treatment of neuropathic pain.

In another aspect, the present invention provides the use of a compound of formula (I) as defined herein, or a pharmaceutically acceptable salt or solvate thereof, or a pharmaceutical composition as defined herein, in the manufacture of a medicament for use in the treatment of chronic neuropathic pain.

In one embodiment of each of the above methods, the patient is a warm blooded animal.

In another embodiment of each of the above methods, the patient is a human.

Chronic pain is often considered as any pain lasting more than 12 weeks. Whereas acute pain is a normal sensation that is part of a rapid warning relay instructing the motor neurons of the central nervous system to minimize detected physical harm, chronic pain is very different. Chronic pain serves no biologic function as it is not a symptom of a disease process but is a disease process itself. Chronic pain persists often for months or even longer.

Chronic pain may arise from an initial injury, such as a back sprain, or there may be an ongoing cause, such as illness. However, there may also be no clear cause. Other health problems, such as fatigue, sleep disturbance, decreased appetite, and mood changes, often accompany chronic pain. Chronic pain may limit a person's movements, which can reduce flexibility, strength, and stamina. This difficulty in carrying out important and enjoyable activities can lead to disability and despair.

In one embodiment, the chronic pain is chronic pain associated with one or more of lower pain back, arthritis, nerve damage, cancer and neurodegenerative disease. In another embodiment, the chronic pain is chronic pain associated with diabetes, arthritis, migraine, fibromyalgia, cancer, shingles, sciatica, and previous trauma or injury involving nerve damage. In another embodiment, the chronic pain is iatrogenic chronic pain.

Neuropathic pain is produced by damage to the neurons in the peripheral and central nervous systems and involves sensitisation of these systems. In peripheral sensitization, there is an increase in the stimulation of peripheral nociceptors that amplifies pain signals to the central nervous system. In central sensitization, neurons that originate in the dorsal horn of the spinal cord become hyperstimulated, increasing pain signals to the brain and thereby increasing pain sensation. It is most commonly associated with chronic allodynia and hyperalgesia. In contrast to neuropathic pain, inflammatory pain is associated with damage to tissue and the resulting inflammatory process.

In one embodiment, the neuropathic pain may be selected from neuropathic pain associated operations (such as amputation), chemotherapy, infection and any other (previous) trauma or injury involving nerve damage.

Routes of Administration

The compounds of formula (I) or pharmaceutical composition thereof may be administered to a patient by any convenient route of administration, whether systemically/peripherally or topically (i.e. at the site of desired action).

Routes of administration include, but are not limited to, oral (e.g, by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

Combination Therapies

The compounds of formula (I) may be administered as a sole therapy in the methods of the invention. Alternatively, the methods of the invention may further comprise the administration of one or more additional therapeutic agents (in addition to a compound of formula (I)).

For example, the methods defined hereinbefore may involve the administration of a compound of formula (I) as a sole therapy or may involve, in addition to the compound of formula (I), the administration of one or more additional analgesic and/or anti-inflammatory agents. Examples of suitable medicaments include non-steroidal anti-inflammatory drugs and opiate analgesics.

Such conjoint treatment may be achieved by way of the simultaneous, sequential or separate dosing of the individual components of the treatment. Such combination products employ the compounds of formula (I) within the dosage range described hereinbefore and the other pharmaceutically-active agent within its approved dosage range.

EXAMPLES

Example 1—Synthesis of (3,5-Di-tert-butyl-4-hydroxyphenyl)(morpholino)methanone

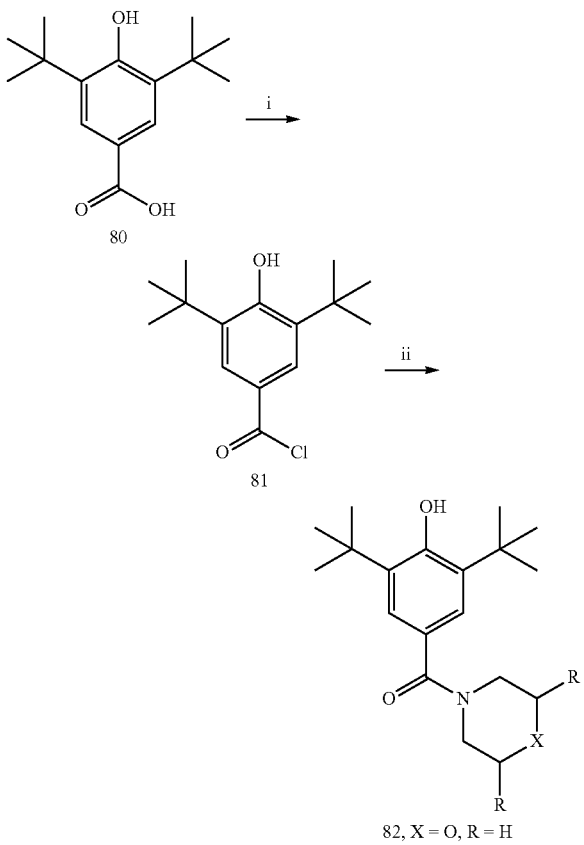

Commercially available 3,5-di-tert-butyl-4-hydroxybenzoic acid (2 g, 8.5 mmol) was reacted with oxalyl chloride (1.4 mL, 17 mmol) and DMF (cat.) in DCM at room temperature for two hours to afford the product as a pale yellow oil. The product from this reaction was not isolated and was carried through crude.

3,5-Di-tert-butyl-4-hydroxybenzoyl chloride (1 g, 3.7 mmol) was reacted with morpholine (0.5 mL, 5.6 mmol) according to general procedure A. The crude product was purified by column chromatography (EtOAc/n-Hexane) to afford the product as an off white solid (957 mg, 81% yield). mp=174-176° C.: $^1$H NMR (400 MHz, CDCl$_3$) δ 7.24 (s, 2H), 5.43 (s, 1H), 3.71 (s, 8H), 1.44 (s, 18H). $^{13}$C NMR (101 MHz, CDCl$_3$) δ 171.98, 155.70, 136.06, 126.20, 124.86, 67.30, 34.70, 30.38. MS [M+Na]$^+$:C$_{19}$H$_{29}$NO$_3$ requires: 342.2045, found: 342.2056. CHN requires C: 71.44%, H: 9.15%, N: 4.38, found C: 71.03%, H: 9.13%, N: 4.28%.

General Procedure A

The appropriate amine (1.2 eq) was added to a stirred solution of the acid chloride (1.0 eq) dissolved in DCM (10 mL/g). Et$_3$N (1.5 eq) was added and the resulting solution was allowed to stir at room temperature for 1.5 hours. The reaction was monitored by TLC and upon completion the reaction mixture was quenched with H$_2$O (50 mL) and extracted with EtOAc (3×50 mL). The combined organic extracts were washed with Na$_2$CO$_3$, dried over MgSO$_4$ and the solvent was removed under vacuum.

Example 2—In Vivo Pain Model

Protocol for study of compounds in a model of neuropathic pain: reversal of tactile allodynia.

Summary
1) In rats a peripheral neuropathy was induced by partial ligation of the sciatic nerve in one hind limb.
2) Two weeks (12-15 days) after induction of peripheral neuropathy stable mechanical (tactile) allodynia was induced in the hind paw of the affected limb.
3) Five treatment groups of male SD rats (n=8) were used: vehicle control (drug formulation), 3 drug doses, and a positive control, lamotrigine (30 mg/kg). Animals were randomized between groups and the experiment was carried out using blinded conditions. The study was split with n=4/group in each experiment.
4) Baseline behavioural measurements were obtained prior to surgery and at intervals post-surgery. Predose behavioural measurements were obtained by measuring paw withdrawal thresholds 12-15 days following nerve ligation.
5) Compound efficacy was determined by measuring paw withdrawal thresholds at specified intervals following vehicle/compound treatment.

Animals

All animal procedures were carried out in accordance with the UK Animals (Scientific Procedures) Act 1986 and associated guidelines. Animals were maintained in a controlled lighting environment and given food and water ad libitum. Male Sprague Dawley rats (120-140 g at time of surgery) were used.

Drug Administration

Rats were fasted overnight with free access to water and fed 4 hours post-dose.

Tests compounds as well as lamotrigine (30 mg/kg, volume: 10 ml/kg)) were prepared in the designated formulation (10% DMSO, Solutol HS 15/80% and 0.9% saline for p.o. administration) and administered via the chosen route.

Induction of Neuropathic Tactile Allodynia

Allodynia was examined in the model of neuropathic pain induced by partial ligation of the sciatic nerve as described by Seltzer et al (1990). Rats were anaesthetised (isoflurane/O$_2$ inhalation), the left sciatic nerve was exposed at mid-thigh level through a small incision and ⅓ to ½ of the nerve thickness tightly ligated within a 7.0 silk suture. The wound was closed with skin clips. Animals were allowed to recover and compounds administered 12-15 days following surgery.

Behavioural Tests

Tactile allodynia was assessed by measuring withdrawal thresholds to calibrated von Frey hairs. As a force higher than 15 g can lift the paw as well as eliciting a response, 15 g represented the cut off point. Animals were placed into a perspex chamber with metal grid floor giving access to the underside of their paws and allowed to acclimatise prior to the start of the experiment. Tactile allodynia was tested by touching the plantar surface of the hind paw with von Frey hairs in ascending order of force for up to 6 seconds. A positive response was noted if the paw is sharply withdrawn or there was flinching upon removal of the hair. Once a positive withdrawal response had been established, the paw was re-tested, starting with the next descending von Frey hair until no response occurred. The lowest amount of force required to elicit a response was recorded as the paw withdrawal threshold (in grams).

Data were also expressed as percentage of the maximum possible effect (% MPE) defined as:

Allodynia was measured on both the ipsilateral (ligated) and contralateral (non-ligated) paw prior to (pre-dose) and at a set time point following compound or vehicle administration (post-dose). Treatment groups were randomised and blinded. Groups of eight rats were used.

Predose behavioural measurements were obtained by measuring paw withdrawal thresholds 12-15 days following nerve ligation; before the initiation of drug treatment.

Compound/vehicle were administered at specified doses. Following treatment, further readings were taken; 1, 3, 6 and 24 hour after p.o. administration.

Cold sensitivity was assessed using a commercially available cold-plate (Ugo Basile, Milan). The cold-plate was set according to pre-determined calibration data using a surface temperature probe to correlate set temperature to actual surface temperature over a wide temperature range (−5° C. to 26° C.). The cold plate was allowed to stabilize for 5 minutes at the set temperature prior to testing. Paw withdrawal latencies were determined with the cold-plate set at 10° C. The animals were lightly restrained and each hind paw in turn placed onto the surface of the cold-plate. The end point was taken as the withdrawal of the paw and recorded as the withdrawal latency for the ipsilateral and the contralateral paw. A maximum cut-off of 30 seconds was used for each paw.

Statistical Analysis

Raw data were analysed using parametric statistical tests, including one-way analysis of variance (ANOVA) followed by Tukey's post hoc test repeated measures of ANOVA. $P<0:05$ was set as the level of statistical significance. Reference: Seltzer Z, Dubner R, Shir Y. A novel behavioural model of neuropathic pain disorders produced in rats by partial sciatic nerve injury. Pain 1990; 43:205±218.

Results

Figure 2:
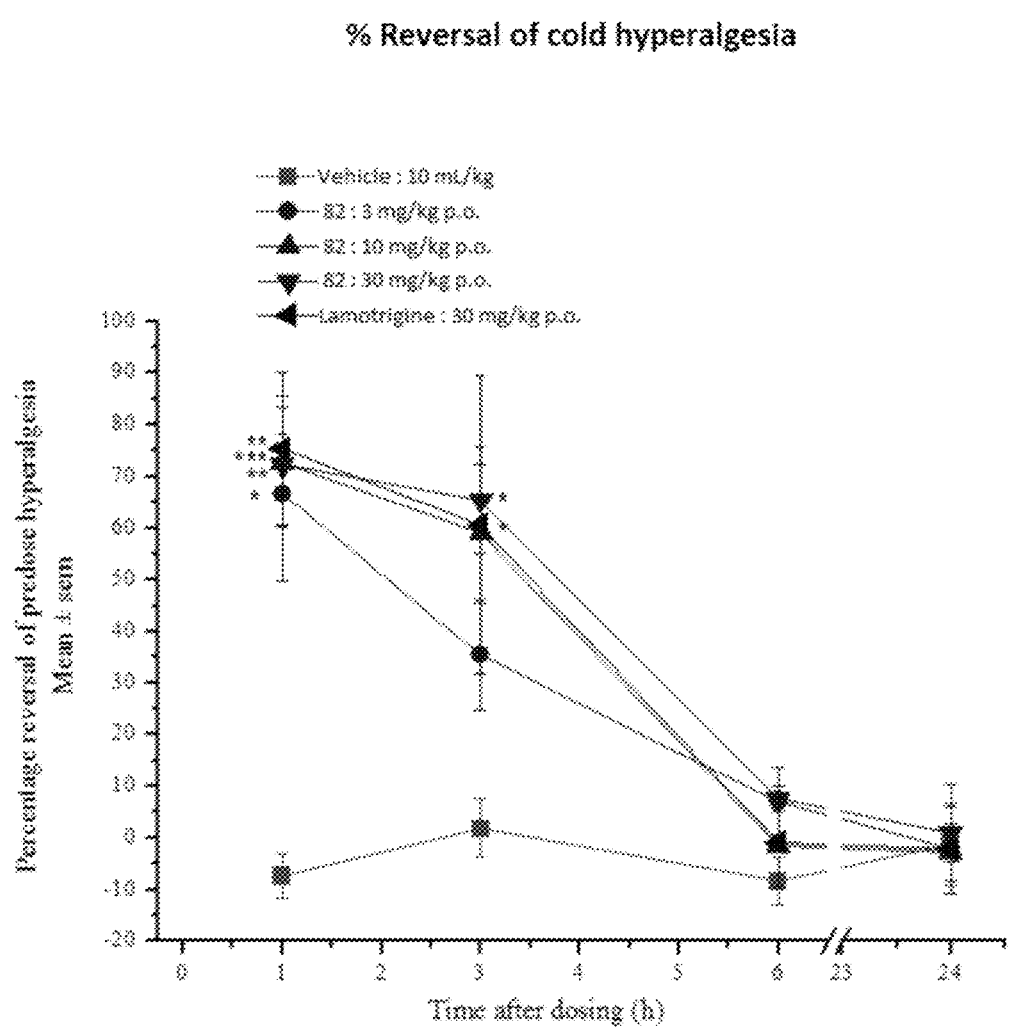
FIG. 2 shows the effect of compound 82 on ipsilateral paw withdrawal thresholds to a cold (10° C.) stimulus in neuropathic rats in comparison with lamotrigine. Fasted, male, Wistar rats. n=6/group. Vehicle: 10% DMSO/10% Solutol HS15/80% saline. 10 ml/kg p.o. One-way ANOVA, comparison with time-matched vehicle group using Tukey's HSD test, *$p<0.05$, $p<0.01$, *$p<0.001$.

The results for the tactile allodynia and cold hyperalgesia tests are shown in FIGS. 1 and 2.

(3,5-Di-tert-butyl-4-hydroxyphenyl)(morpholino) methanone (82) produced a marked and long-lasting reversal of both the cold (10° C. cold plate) and mechanical (paw pressure) parameters. All three doses of the compound 82 showed good and dose-related efficacy. Peak reversal of tactile allodynia of 72% occurred at 1 h following a 30 mg/kg dose of compound 82, similar to the positive control, lamotrigine. With result to cold hyperalgesia, a peak reversal of 74% occurred at 1 h following a 30 mg/kg dose of compound 82, similar to the positive control, lamotrigine.

Compound 82 showed a significant increase in contralateral paw withdrawal thresholds to mechanical pressure and increased contralateral paw withdrawal latencies to cold.

There were no apparent drug-induced behavioural side effects.

Example 3—In Vitro Characterization of Glycine Receptor Activity

Oocyte Preparation and Electrophysiology

Oocytes were surgically removed from adult female *Xenopus laevis* clawfrogs anaesthetized by immersion in 0.3% tricaine in water (w/v). All protocols were approved by the local animal care and use committee (II25.3-19c20/15; RP Darmstadt, Germany). Stage V and VI Oocytes were dissected and stored in sterile-filtered ND96 medium (composition in mM: 96 NaCl, 2 KCl, 1 CaCl, 1 MgCl, 5 HEPES, pH 7.4) containing gentamycin (50 µg/mL). The oocytes were isolated and enzymatically and maintained as described previously (Grudzinska et al., 2005). Oocytes were injected with 5 ng of cRNA using a Drummond microinjector (Drummond Scientific, Broomall, USA) and incubated in ND96 for 24 h at 18° C. before electrophysiological recording. Two-electrode voltage-clamp (TEVC) with microelectrodes containing 3 M KCl was performed in bath solution at a holding potential of −70 mV as described previously (Laube et al., 2000). Currents were acquired at 200 Hz with a Geneclamp 500B amplifier, a Digidata 1322A digitizer and Clampex 9.2 software (Molecular Devices). Gycine, dissolved in bath solution, was applied alone or after 30 s pre-application of propofol, also dissolved in bath solution. Formation of heteromeric α1β GlyRs was verified by lindane as described previously (Islam and Lynch, 2012). For direct activation, propofol or 4-chloropropofol were applied in the absence of glycine. All experiments were performed at room temperature.

Data Analysis

Currents were measured with Clampfit 9.2 software (Molecular Devices), Results were analyzed using the KaleidaGraph program (Synergy Software, Reading, Pa.) and GraphPad Prism version 5.0 (GraphPad Software Inc., San Diego, Calif.). Peak current responses to glycine were plotted against agonist concentration and fit with variable slope non-linear regression to establish agonist $EC_{20}$ and $EC_{50}$ parameters. For propofol and 4-chloropropofol modulation, responses to $EC_{20}$ glycine after application were analyzed as described previously (Lynagh and Laube, 2014); mean±standard error of the mean (SEM) are reported. Drug-induced fold enhancement or remaining fractional current were fit with variable slope non-linear regression (Prism 4), giving $EC_{50}$ or $IC_{50}$ parameters for each individual experiment. For strychnine inhibition, responses to propofol after strychnine application were divided by the response without strychnine, giving the remaining fractional current indicated. Biphasic propofol- and 4-chloropropofol-induced current changes were fit with a biphasic Hill equation as described previously (Grudzinska et al., 2005). In calculating increases in current for the low affinity phase, the maximal increase in current of the high affinity phase was subtracted from each data point. In all experiments, each construct was tested in at least two batches of oocytes. Means for mutants were compared with means for wild-type by unpaired Student's t test. Differences with a P value less than 0.05 were considered significant. The results are shown in FIG. 1 for the compound of Example 1 (LT-01-25).

Results

The following $EC_{50}$ data was obtained for the compound of Example 1:

| Compound | α1 glycine $EC_{50}$ (nM) |
|---|---|
| 82 | 0.46 +/− 0.2 |

Example 4—Molecular Modelling

Molecular docking studies were carried out using the crystal structure of α1 GlyR transmembrane structure (4X5T), residues missing from the crystal were modelled using SCWRL4.0 (G. G. Krivov, M. V. Shapovalov, and R. L. Dunbrack, Jr. Improved prediction of protein side-chain conformations with SCWRL4. Proteins (2009)). Small molecules structures were generated and energy minimized using molecular mechanics in Spartan'14 (Wavefunction Inc., Irvine, Calif., USA; 1991-2009). Calculations were carried out with GOLD 5.2 (CCDC Software Limited, Cambridge, UK), Hydrogen atoms were added to the protein, and all crystallographic water molecules were removed. Default settings were used throughout with the exception that 50 docking poses were generated, search efficiency was set to 200% and the early termination option was disabled. The docking cavity defined as a 11 Å radius around the c-alpha of S296. CHEMPLP fitness function was used to perform the docking. CHEMPLP is used to model the steric complementarity between the protein and the ligand together with the distance- and angle-dependent hydrogen bonding terms.

Each of the following compounds below were predicted to bind strongly and in a similar fashion as described below in the tight aromatic interface of TM4 with residues of TM1 and TM3.

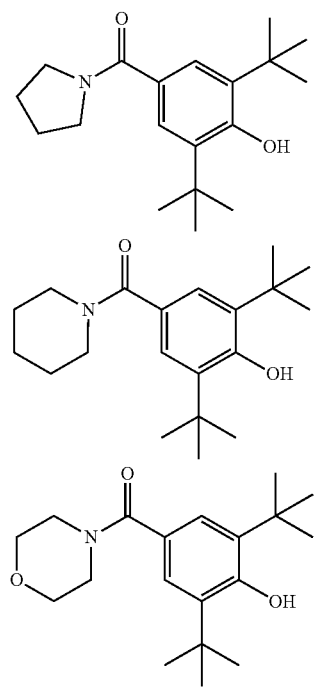

-continued

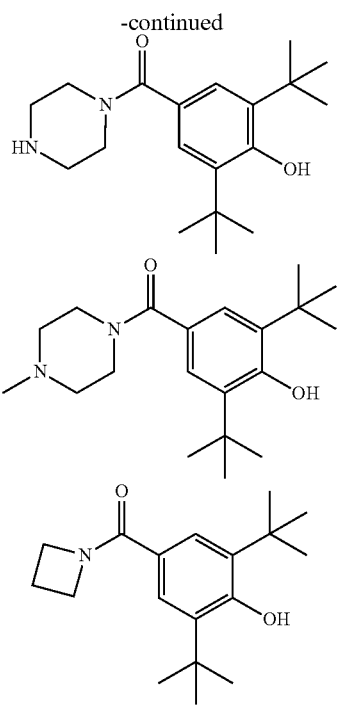

Figure 3:
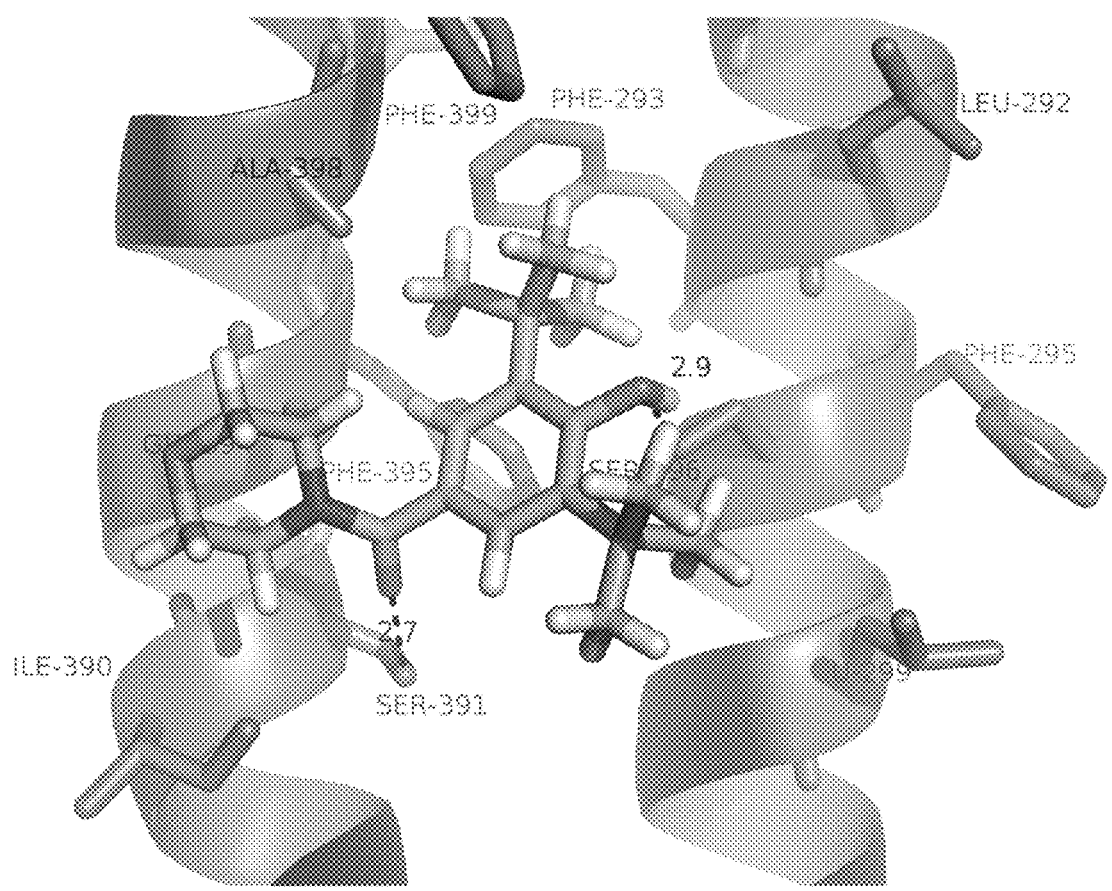
FIG. 3 shows the predicted binding pose of compound 82 in the crystal structure of α1 GlyR transmembrane structure (4X5T). Protein backbone rendered as a blue cartoon. Residues within 4 Ångstrom of compound rendered as sticks (carbon—grey, Oxygen—red), compound 82 rendered as sticks (Carbon—green, Nitrogen—blue, Oxygen—red, Hydrogen—white). Hydrogen bond indicated by black dotted line with distance in Ångstrom.

There are several cooperative non-covalent interactions which drive the binding process for these compounds. For example there is a notable hydrogen bond between Ser296 and the hydroxy moiety and another hydrogen bond between the carbonyl oxygen and Ser391. In addition, there are hydrophobic contacts between the t-butyl groups and Phe293, Phe399 and Leu299 (FIG. 3).

Figure 4:
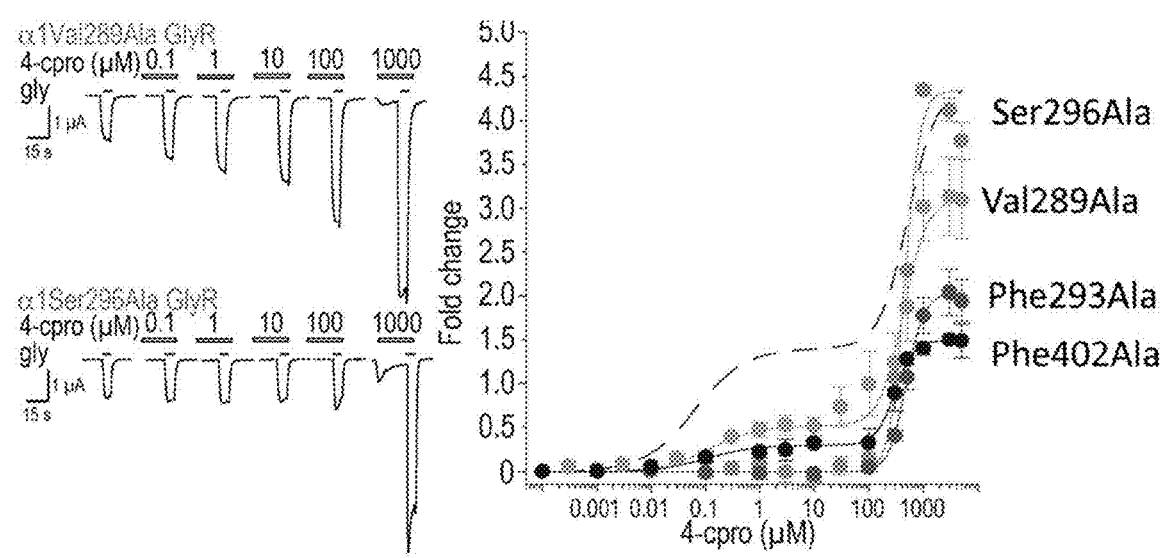
FIG. 4 shows the results of mutational analysis studies.

Mutational analysis data is highly supportive that region surrounding S296 is the high affinity binding site for this family of compounds (see FIG. 4).

Ser296 replaced by Ala results in high affinity binding abolished.

Phe293 replaced by Ala results in high affinity binding abolished.

Phe402 replaced by Ala results in high affinity binding reduced 2 fold.

Val289 replaced by Ala results in high affinity binding reduced 6 fold.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise paragraphed. No language in the specification should be construed as indicating any non-paragraphed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the paragraphs appended hereto as permitted by applicable law.

The invention claimed is:

1. A method of treating pain by relieving or attenuating pain in a patient in need of such treatment, said method comprising administering to said patient a therapeutically effective amount of a compound of formula (I) or a pharmaceutically acceptable salt or solvate thereof:

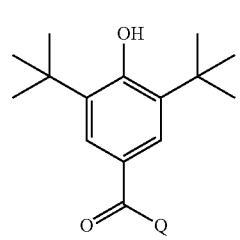

(I)

wherein:
Q is selected from:

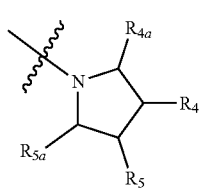

(iia)

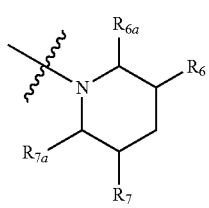

(iiia)

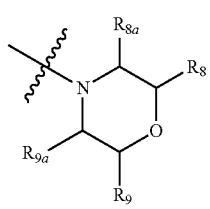

(iva)

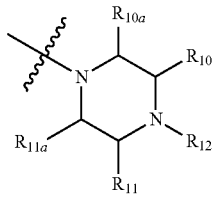

(va)

wherein:
$R_4$, $R_{4a}$, $R_5$ and $R_{5a}$ are each independently selected from hydrogen, halo, hydroxy, a linear or branched, saturated or unsaturated (1-8C) aliphatic group, an —O(1-8C) alkyl group, an amino group, a —CO—$NH_2$ group, a —CO—NH-(1-8C alkyl) group, a —CO—N-(1-8C alkyl)$_2$ group an —NH—CO-(1-8C alkyl) group, a carboxy group, and an aryl group, wherein said aliphatic group, —O(1-8C) alkyl group, —CO—NH-(1-8C alkyl) group, —CO—N-(1-8C alkyl)$_2$ group, —NH—CO-(1-8C alkyl) group and aryl group may be optionally substituted with one or more groups selected from halo, (1-4C) alkyl, and hydroxy;

$R_6$, $R_{6a}$, $R_7$ and $R_{7a}$ are each independently selected from hydrogen, halo, hydroxy, a linear or branched, saturated or unsaturated (1-8C) aliphatic group, an —O(1-8C) alkyl group, an amino group, a —CO—NH$_2$ group, a —CO—NH-(1-8C alkyl) group, a —CO—N-(1-8C alkyl)$_2$ group an —NH—CO-(1-8C alkyl) group, a carboxy group, and an aryl group, wherein said aliphatic group, —O(1-8C) alkyl group, —CO—NH-(1-8C alkyl) group, —CO—N-(1-8C alkyl)$_2$ group, —NH—CO-(1-8C alkyl) group and aryl group may be optionally substituted with one or more groups selected from halo, (1-4C) alkyl, and hydroxy;

$R_8$, $R_{8a}$, $R_9$ and $R_{9a}$ are each independently selected from hydrogen, halo, hydroxy, a linear or branched, saturated or unsaturated (1-8C) aliphatic group, an —O(1-8C) alkyl group, an amino group, a —CO—NH$_2$ group, a —CO—NH-(1-8C alkyl) group, a —CO—N-(1-8C alkyl)$_2$ group an —NH—CO-(1-8C alkyl) group, a carboxy group, and an aryl group, wherein said aliphatic group, —O(1-8C) alkyl group, —CO—NH-(1-8C alkyl) group, —CO—N-(1-8C alkyl)$_2$ group, —NH—CO-(1-8C alkyl) group and aryl group may be optionally substituted with one or more groups selected from halo, (1-4C) alkyl, and hydroxy;

$R_{10}$, $R_{10a}$, $R_{11}$ and $R_{11a}$ are each independently selected from hydrogen, halo, hydroxy, a linear or branched, saturated or unsaturated (1-8C) aliphatic group, an —O(1-8C) alkyl group, an amino group, a —CO—NH$_2$ group, a —CO—NH-(1-8C alkyl) group, a —CO—N-(1-8C alkyl)$_2$ group an —NH—CO-(1-8C alkyl) group, a carboxy group, and an aryl group, wherein said aliphatic group, —O(1-8C) alkyl group, —CO—NH-(1-8C alkyl) group, —CO—N-(1-8C alkyl)$_2$ group, —NH—CO-(1-8C alkyl) group and aryl group may be optionally substituted with one or more groups selected from halo, (1-4C) alkyl, and hydroxy; and $R_{12}$ is selected from hydrogen, (1-6C)alkyl and (1-6C) haloalkyl; and wherein:
∿∿∿ indicates the point of attachment to the C(=O) moiety of the compound of formula I.

2. The method of claim 1 wherein:
$R_4$, $R_{4a}$, $R_5$ and $R_{5a}$ are each independently selected from hydrogen, halo, methyl, hydroxymethyl, CF$_3$ and OCF$_3$;
$R_6$, $R_{6a}$, $R_7$ and $R_{7a}$ are each independently selected from hydrogen, halo, methyl, hydroxymethyl, CF$_3$ and OCF$_3$;
$R_8$, $R_{8a}$, $R_9$ and $R_{9a}$ are each independently selected from hydrogen, methyl, CF$_3$ halo, hydroxymethyl and OCF$_3$;
$R_{10}$, $R_{10a}$, $R_{11}$ and $R_{11a}$ are each independently selected from hydrogen, methyl, CF$_3$ halo, hydroxymethyl and OCF$_3$; and
$R_{12}$ is selected from hydrogen, (1-4C)alkyl or (1-4C) haloalkyl.

3. The method of claim 1, wherein $R_4$, $R_{4a}$, $R_5$ and $R_{5a}$ are each independently selected from hydrogen, fluoro or methyl.

4. The method of claim 3, wherein $R_4$ and $R_5$ are both hydrogen.

5. The method of claim 3, wherein one of $R_4$ and $R_5$ is fluoro or methyl and the other is hydrogen.

6. The method of claim 3, wherein $R_{4a}$ and $R_{5a}$ are both hydrogen.

7. The method of claim 1, wherein $R_6$, $R_{6a}$, $R_7$ and $R_{7a}$ are each independently selected from hydrogen, fluoro or methyl.

8. The method of claim 7, wherein $R_6$ and $R_7$ are both hydrogen.

9. The method of claim 7, wherein one of $R_6$ and $R_7$ is fluoro or methyl and the other is hydrogen.

10. The method of claim 7, wherein $R_{6a}$ and $R_{7a}$ are both hydrogen.

11. The method of claim 1, wherein $R_8$, $R_{8a}$, $R_9$ and $R_{9a}$ are each independently selected from hydrogen or methyl.

12. The method of claim 11, wherein $R_8$ and $R_9$ are both hydrogen.

13. The method of claim 11, wherein one of $R_8$ and $R_9$ is methyl and the other is hydrogen.

14. The method of claim 11, wherein $R_{8a}$ and $R_{9a}$ are both hydrogen.

15. The method of claim 1, wherein $R_{10}$, $R_{10a}$, $R_{11}$ and $R_{11a}$ are each independently selected from hydrogen, fluoro or methyl.

16. The method of claim 15, wherein one of $R_{10}$ and $R_{11}$ is fluoro or methyl and the other is hydrogen.

17. The method of claim 15, wherein $R_{10}$ and $R_{11}$ are both hydrogen.

18. The method of claim 15, wherein $R_{10a}$ and $R_{11a}$ are both hydrogen.

19. The method of claim 1, wherein $R_{12}$ is methyl.

20. The method of claim 1, wherein the compound of formula (I) is selected from the group consisting of
(4-(hydroxy)-3,5-di-tert-butylphenyl)(morpholino)methanone;
(R)-(4-(hydroxy)-3,5-di-tert-butylphenyl)(2-methylmorpholino)methanone;
(4-(benzyloxy)-3,5-di-tert-butylphenyl)(piperidin-1-yl)methanone; and
(4-Hydroxy-3-5-di-tert-butylphenyl)(4-methylpiperazin-1-yl)methanone;
or a pharmaceutically acceptable salt or solvate thereof.

21. The method claim 1, wherein the compound of formula (I) is (4-(hydroxy)-3,5-di-tert-butylphenyl)(morpholino)methanone

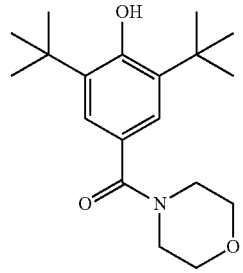 [SMILES: CC(C)(C)c1cc(C(=O)N2CCOCC2)cc(C(C)(C)C)c1O]

or a pharmaceutically acceptable salt or solvate thereof.

22. The method of claim 1, wherein the compound of formula (I) or a pharmaceutically acceptable salt or solvate thereof is administered as a pharmaceutical composition comprising said compound, or a pharmaceutically acceptable salt thereof, in admixture with a pharmaceutically acceptable diluent or carrier.

\* \* \* \* \*